US00PP23276P2

(12) United States Plant Patent
Konst

(10) Patent No.: US PP23,276 P2
(45) Date of Patent: Dec. 25, 2012

(54) ***ALSTROEMERIA* PLANT NAMED 'KONCAMAMBO'**

(50) Latin Name: *Alstroemeria hybrida*
Varietal Denomination: Koncamambo

(75) Inventor: Johannes Wilhelmus Maria Konst, GA Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 98 days.

(21) Appl. No.: 13/065,246

(22) Filed: Mar. 17, 2011

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu

(74) *Attorney, Agent, or Firm* — C. A. Whealy

(57) ABSTRACT

A new and distinct cultivar of *Alstroemeria* plant named 'Koncamambo', characterized by its compact and mounding plant habit; sturdy and strong plants; vigorous growth habit; orange-colored flowers; and good garden performance.

2 Drawing Sheets

Botanical designation: *Alstroemeria hybrida.*
Cultivar denomination: 'KONCAMAMBO'.

BACKGROUND OF THE INVENTION

The present invention relates to a new and distinct cultivar of *Alstroemeria* plant, botanically known as *Alstroemeria hybrida*, typically grown as a potted garden *Alstroemeria*, and hereinafter referred to by the name 'Koncamambo'.

The new *Alstroemeria* plant is a product of a planned breeding program conducted by the Inventor in Nieuwveen, The Netherlands. The objective of the breeding program is to create new compact potted garden *Alstroemeria* plants that are early and freely flowering and have attractive leaf and flower coloration.

The new *Alstroemeria* plant originated from a cross-pollination made by the Inventor in Nieuwveen, The Netherlands on Sep. 11, 2006 of a proprietary *Alstroemeria hybrida* selection identified as code number 20139-16, not patented, as the female, or seed, parent with a proprietary *Alstroemeria hybrida* selection identified as code number 24274-1, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands on Aug. 18, 2008.

Asexual reproduction of the new *Alstroemeria* plant by in vitro rhizogenesis in a controlled greenhouse environment in Nieuwveen, The Netherlands since Aug. 18, 2008 has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Koncamambo'. These characteristics in combination distinguish 'Koncamambo' as a new and distinct cultivar of *Alstroemeria* plant:

1. Compact and mounding plant habit.
2. Sturdy and strong plants.
3. Vigorous growth habit.
4. Orange-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of the female parent selection.
2. Plants of the new *Alstroemeria* and the female parent selection differ in flower color as plants of the female parent selection have light red-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* have smaller leaves than plants of the male parent selection.

Plants of the new *Alstroemeria* can be compared to plants of the *Alstroemeria hybrida* 'Konpride', disclosed in U.S. Plant Pat. No. 20,050. In side-by-side comparisons conducted in Nieuwveen, The Netherlands, plants of the new *Alstroemeria* differed from plants of 'Konpride' in the following characteristics:

1. Plants of the new *Alstroemeria* were shorter and broader than plants of 'Konpride'.
2. Plants of the new *Alstroemeria* had smaller flowers than plants of 'Konpride'.
3. Flowers of plants of the new *Alstroemeria* had narrower perianth segments than flowers of plants of 'Konpride'.
4. Plants of the new *Alstroemeria* and 'Konpride' differed in flower color as plants of 'Konpride' had bright pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Koncamambo' grown in container.

The photograph on the second sheet is a close-up view of a typical flowering plant of 'Koncamambo'.

DETAILED BOTANICAL DESCRIPTION

The aforementioned photographs and following observations and measurements describe plants of the new *Alstroemeria* grown in a polyethylene-covered greenhouse during the summer in 19-cm containers in Nieuwveen, The Netherlands and under conditions and practices typical of commercial potted *Alstroemeria* production. During the production of the plants, day temperatures ranged from 6° C. to 35° C. and night temperatures ranged from 6° C. to 20° C. Plants were 36 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncamambo'.

Parentage:

- *Female, or seed, parent*.—Proprietary *Alstroemeria hybrida* selection identified as code number 20139-16, not patented.
- *Male or pollen parent*.—Proprietary *Alstroemeria hybrida* selection identified as code number 24274-1, not patented.

Propagation:

- *Type*.—In vitro rhizogenesis.
- *Root description*.—Thick, fleshy; color, close to 159D.
- *Rooting habit*.—Freely branching; dense.
- *Rhizome description*.—Shape: Elongate; rounded. Length: About 3 cm to 7 cm. Diameter: About 8 mm. Texture: Smooth. Color: Close to 159D.

Plant description:

- *Plant habit*.—Compact and mounded; freely branching, bushy appearance; sturdy and strong plants; vigorous growth habit.
- *Plant height*.—About 30 cm.
- *Plant diameter* (*area of spread*).—About 43 cm.

Stem description:

- *Aspect*.—Upright to somewhat outwardly spreading.
- *Internode length*.—About 0.5 cm to 3 cm.
- *Strength*.—Strong, sturdy.
- *Texture*.—Smooth, glabrous.
- *Color*.—Close to 144A; towards the base, close to 187B; occasionally towards the apex, close to 187B.

Foliage description:

- *Arrangement*.—Alternate; below the peduncles in a single whorl; all leaves sessile.
- *Length*.—About 2.5 cm to 11.5 cm.
- *Width*.—About 0.8 cm to 2.6 cm.
- *Shape*.—Lanceolate.
- *Apex*.—Acute.
- *Base*.—Attenuate.
- *Margin*.—Entire.
- *Texture, upper and lower surfaces*.—Smooth, glabrous.
- *Venation pattern*.—Parallel.
- *Color*.—Developing leaves, upper and lower surfaces: Close to 141A. Fully expanded leaves, upper surface: Close to 141B; venation, close to 137A. Fully expanded leaves, lower surface: Close to 137A; venation, close to 144A.

Flower description:

- *Flower type and habit*.—Single cup-shaped flowers arranged in compound umbels; flowers face upright to outwardly; freely flowering habit; about two to six flowers per inflorescence; about 30 to 60 flowers develop per plant.
- *Natural flowering season*.—Flowering continuous from the late spring until the autumn in The Netherlands.
- *Fragrance*.—None detected.
- *Flower longevity on the plant*.—About one to three weeks; flowers not persistent.
- *Flower longevity as a cut flower*.—About one to two weeks; flowers not persistent.
- *Flower buds*.—Length: About 3.5 cm. Diameter: About 1.2 cm. Shape: Ovoid. Color: Close to 53A; towards the apex, close to 137A.
- *Umbel height*.—About 12 cm.
- *Umbel diameter*.—About 14 cm.
- *Flower diameter*.—About 4.5 cm.
- *Flower depth* (*height*).—About 5 cm.
- *Perianth*.—Arrangement: Six arranged in two whorls, each whorl with two lateral and one median segments. Size, inner perianth: Length, lateral segments: About 4.5 cm. Width, lateral segments: About 1.2 cm. Length, median segment: About 4 cm. Width, median segment: About 1.1 cm. Size, outer perianth: Length, lateral segments: About 5 cm. Width, lateral segments: About 2.5 cm. Length, median segment: About 5.5 cm. Width, median segment: About 2.2 cm. Shape, inner perianth, lateral and median segments: Lanceolate. Shape, outer perianth, lateral and median segments: Oblanceolate. Apex, inner perianth, lateral and median segments: Acute. Apex, outer perianth, lateral and median segments: Embedded point. Base, inner and outer perianths, lateral and median segments: Attenuate. Margin, inner and outer perianths, lateral and median segments: Entire. Texture, inner and outer perianths, lateral and median segments: Smooth, glabrous. Color, inner perianth: When opening, lateral segments, upper surface: Towards the apex, close to N34B; mid-section, close to 1B; towards the base, close to 22A; spot, close to 53A. When opening, median segment, upper surface: Towards the apex, close to 34A; mid-section, close to 21B; towards the base, close to 24C; spot, close to 53A. When opening, lateral segments, lower surface: Towards the apex, close to 35A; mid-section, close to 1B; towards the base, close to 53A; spot, close to 53A. When opening, median segment, lower surface: Towards the apex, close to 35A; mid-section, close to 17D; towards the base, close to 36A; spot, close to 53A. Fully opened, lateral segments, upper surface: Towards the apex, close to N34B; mid-section, close to 13A; towards the base, close to 22A; spot, close to 53A. Fully opened, median segment, upper surface: Towards the apex, close to 34A; mid-section, close to 21B; towards the base, close to 24C; spot, close to 53A. Fully opened, lateral segments, lower surface: Towards the apex, close to 34A; mid-section, close to 21B; towards the base, close to 24C; spot, close to 53A. Fully opened, median segment, lower surface: Towards the apex, close to 35A; mid-section, close to 17A; towards the base, close to 36A; spot, close to 53A. Color, outer perianth: When opening, lateral segments, upper and lower surfaces: Towards the apex, close to 35C; mid-section, close to 31B; towards the base, close to 24C; at the apex, close to 53A. When opening, median segment, upper and lower surfaces: Towards the apex, close to 35C; mid-section, close to 31B; towards the base, close to 24C; at the apex, close to 53A. Fully opened, lateral and median segments, upper surface: Towards the apex, close to 35C; mid-section, close to 31B; towards the base, close to 24C; at the apex, close to 53A. Fully opened, lateral and median segments, lower surface: Towards the apex, close to 45A; mid-section, close to 28C; towards the base, close to 34C.

*Pedicels*.—Length: About 1.4 cm to 3.2 cm. Diameter: About 2 mm. Strength: Strong. Angle: Erect to about 30° from vertical. Texture: Smooth, glabrous. Color: Close to 146A.

*Reproductive organs*.—Stamens: Quantity per flower: Six. Anther shape: Oval. Anther size: About 2 mm by 7 mm. Anther color: Close to N199A. Pollen amount: Abundant. Pollen color: Close to 166A. Pistils: Quantity per flower: One. Pistil length: About 4 cm. Style length: About 3.2 cm. Style color: Close to 3C. Stigma color: Close to 37A. Ovary color: Close to 146A.

*Fruits*.—Length: About 7 mm. Diameter: About 7 mm. Color: Close to 199A.

*Seeds*.—None observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncamambo' as illustrated and described.

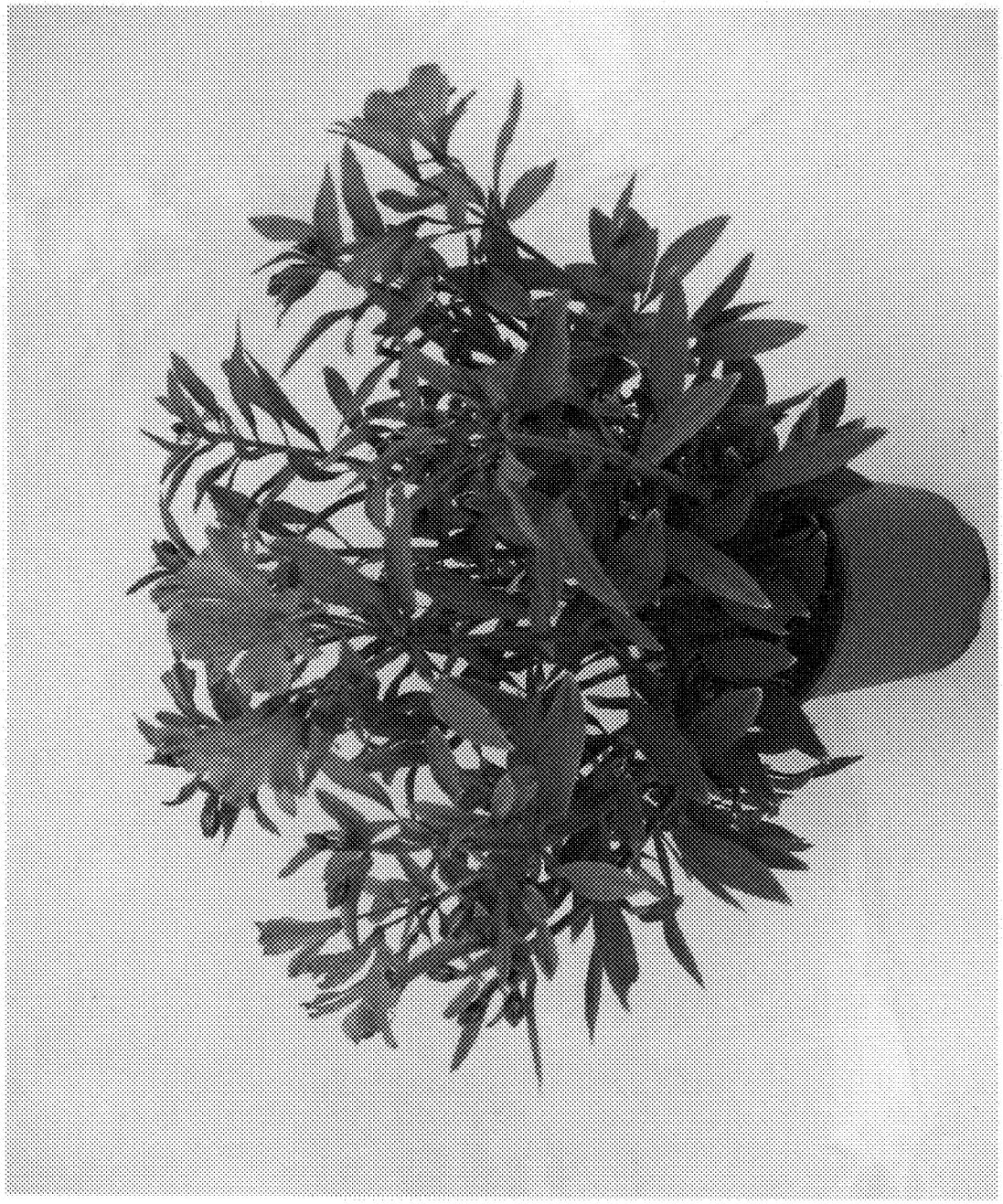

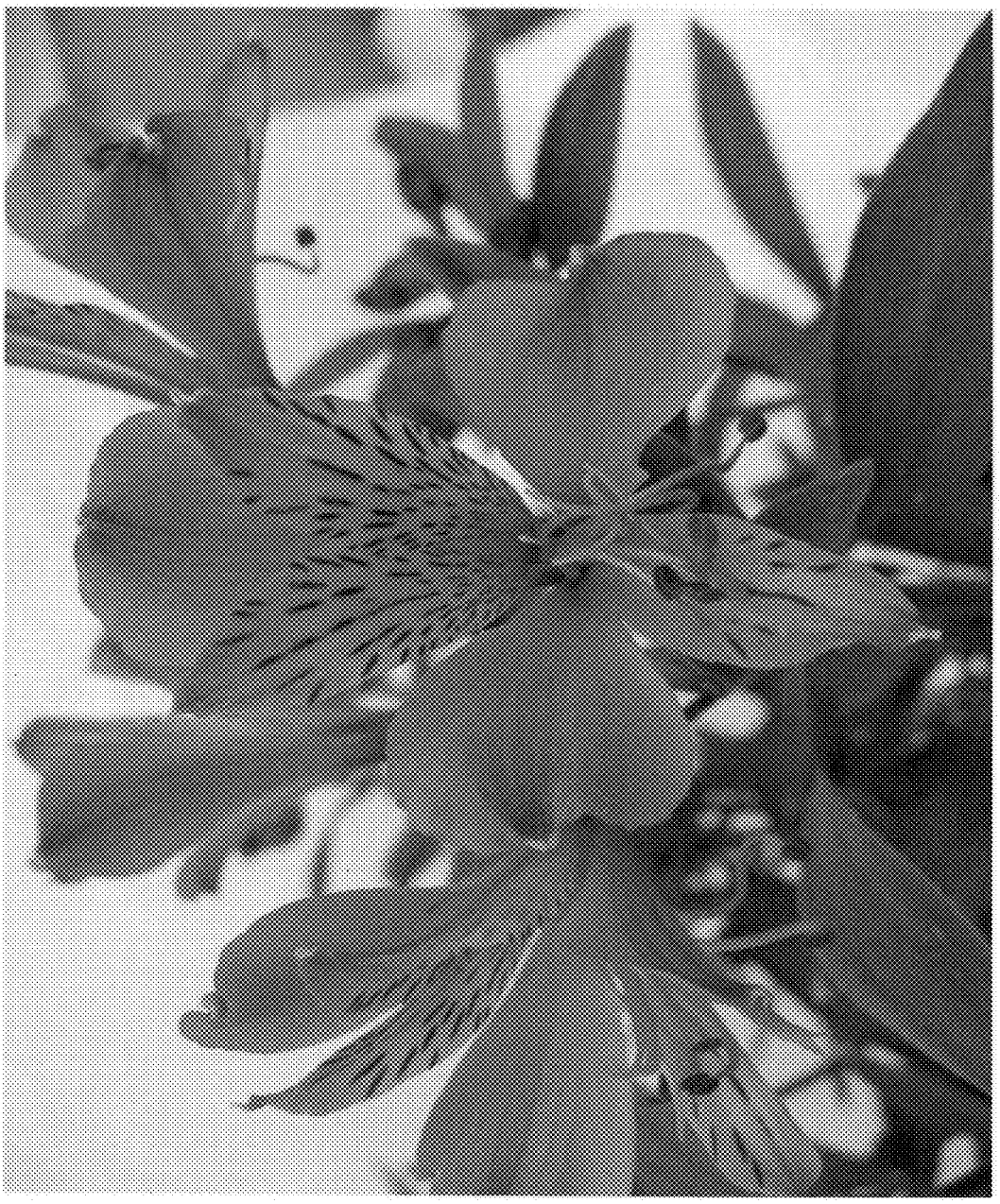

* * * * *